(12) United States Patent
Wortrich

(10) Patent No.: US 6,874,629 B1
(45) Date of Patent: Apr. 5, 2005

(54) CASE FOR MICROKERATOME BLADE

(75) Inventor: Theodore Wortrich, 14762 Bentley Cir., Tustin, CA (US) 92780

(73) Assignee: Theodore Wortrich, Tustin, CA (US)

( * ) Notice: Subject to any disclaimer, the term of this patent is extended or adjusted under 35 U.S.C. 154(b) by 80 days.

(21) Appl. No.: 10/347,413

(22) Filed: Jan. 21, 2003

Related U.S. Application Data

(60) Provisional application No. 60/349,330, filed on Jan. 18, 2002.

(51) Int. Cl.[7] .......................... B23P 19/04; B65D 85/00
(52) U.S. Cl. ...................... 206/349; 206/352; 206/355; 206/363; 206/438; 206/775; 206/804; 29/239
(58) Field of Search ............................... 206/349, 355, 206/352, 363, 438, 804, 775; 29/239

(56) References Cited

U.S. PATENT DOCUMENTS

| | | | |
|---|---|---|---|
| 2,792,108 A | * | 5/1957 | Keller ........................ 206/208 |
| 4,998,334 A | * | 3/1991 | Pemberton et al. ........... 29/239 |
| 5,088,173 A | * | 2/1992 | Kromer et al. ................ 29/239 |
| 5,301,807 A | * | 4/1994 | Donahue ..................... 206/370 |
| 5,528,811 A | * | 6/1996 | Abidin et al. ................. 29/428 |
| 5,727,682 A | * | 3/1998 | Abidin et al. ............... 206/354 |

* cited by examiner

Primary Examiner—Derris H. Banks
Assistant Examiner—Dmitry Suhol
(74) Attorney, Agent, or Firm—Jones, Tullar & Cooper, P.C.; Raymond A. Bogucki

(57) ABSTRACT

A small case for protecting a microkeratome blade while allowing inspection and cleaning of the blade cutting edge incorporates adjacent walls which are hinged together to open and close relative to an inserted microkeratome blade. In position, when the case is closed the blade is set in a recess in one of the walls and held in position by an opposing surface on the other wall. Windows encompassing the cutting edge in each of the walls allow visual inspection and cleaning, if desired. When the case is opened, a converging guide groove extending from a side of one wall into the blade unit and to a point behind the cutting edge allows a surgeon to insert and guide a forceps into the blade unit so that it can be gripped and removed without contacting the cutting edge.

9 Claims, 2 Drawing Sheets

CASE FOR MICROKERATOME BLADE

REFERENCE TO PRIOR APPLICATIONS

This application relies for priority on provisional application Ser. No. 60/349,330 filed Jan. 18, 2002.

FIELD OF THE INVENTION

This invention relates to surgical instrument holders and more specifically to a case for retaining microkeratome blades up to the time of use at the operative site.

BACKGROUND OF THE INVENTION

Microkeratome blades are now widely used for in situ ophthalmic surgeries employing laser correction. In such surgical systems, the eye is drawn into a fixed exposed position so that a cutting blade can move in a curved or linear path across the cornea, tangential to the curve of the eye, and at a preselected depth. The blade thereby cuts a flap of controlled thickness in the cornea across the center of the eye. The flap can then be raised, so that a computer controlled laser beam can be directed against the exposed portion and corneal tissue selectively ablated to introduce the needed optical correction. The flap is then returned back into position on the principal body of the cornea and no further surgical treatment such as a suture is typically needed.

The blades used in these operations are small (about ½ inch in cutting edge length) and are formed as an integrated unit with a small holder or driver, via which the blade can be reciprocated in oscillating fashion. The nature of the incision cut into the cornea is highly dependent upon providing and preserving a precise cutting edge on the blade, inasmuch as an irregular tissue surface, such as a serrated or torn surface resulting from the cut, affects both the vision of the patient and the healing process. In addition at least the cutting edge portion of the blade must be assuredly sterile.

Microkeratome blades are usually used only for a single operation, because of the need for a sharp, uniform cutting edge and the dangers of cross contamination. Prior to use they are conventionally kept in small cases, in sterile condition within an enclosing package. After the sterile package is opened, the blade is withdrawn from its case at the operative site. Prior to extraction of the blade from its case, surgeons often wish to inspect the cutting edge under magnification, and swab the cutting edge to make sure that it is antiseptically clean. The cases heretofore used for these purposes have not permitted complete inspection and treatment of both sides of the cutting edge without removal from the case, and have been structured in such ways as to require special tools or intricate or dexterous manipulation to remove the blade from the case.

SUMMARY OF THE INVENTION

A case for storage and presentation of a microkeratome blade at an operative site comprises a hinged body, which clamps the blade and its driver securely between opposing surfaces. Each of the halves of the hinged body are apertured around the cutting edge of the inserted blade, such as to permit access for visual inspection and, if desired, assured sterilization. The hinged body can be opened by separation of wing-shaped clasps to reveal the blade and driver in retained position. The blade edge is forceps accessible from the side of the case via a tapered opening with converging surfaces which guide the forceps tips to an exposed portion adjacent the blade cutting edge. Thus in a single guided motion a surgeon can grasp and remove the blade by use of conventional forceps without danger of contacting the cutting edge, so as to place the blade and its associated driver into the microkeratome machine. The halves of the body can be molded as an integral unit about a central hinge, with pins on one half engaging mating post holes on the other to permit secure retention that is readily overcome manually when the blade is to be used.

BRIEF DESCRIPTION OF THE DRAWINGS

A better understanding of the invention may be had by reference to the following description, taken in conjunction with the accompanying drawings in which.

DETAILED DESCRIPTION OF THE INVENTION

Figure 1:
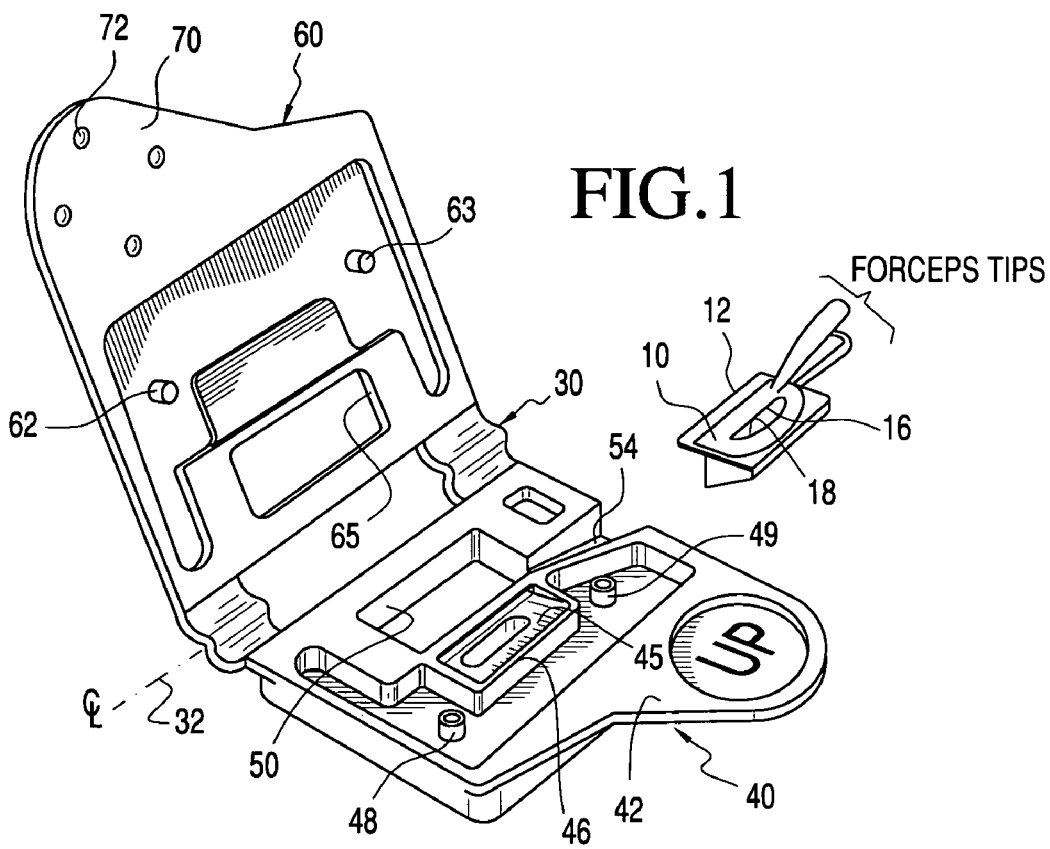
FIG. 1 is a perspective view of an opened protective case for an adjacent microkeratome blade shown held by forceps tips.

Referring now to FIGS. 1–5, a microkeratome blade 10 (FIGS. 1, 2 and 5) has a cutting edge 12 at what will be called its front and a single back edge 14 that is curvilinear in outline. The blade 10 includes an aperture 16 near its back edge in which an upstanding boss part 18 of a triangular (in section) driver 20 is secured. Microkeratome blades typically have a straight front edge although the remaining periphery can be of different shapes, and the driver as well, although the driver forms a three dimensional block that protrudes from the blade surface. In the microkeratome machine, the cutting edge 12 of the blade 10 is driven from side to side by elements acting on a slot (not shown) in the driver 20, as the blade is advanced through the cornea. The triangular-sided driver 20 (best seen in FIG. 5) seats in a mating recess to position and hold the blade 10, as will be described.

Figure 3:
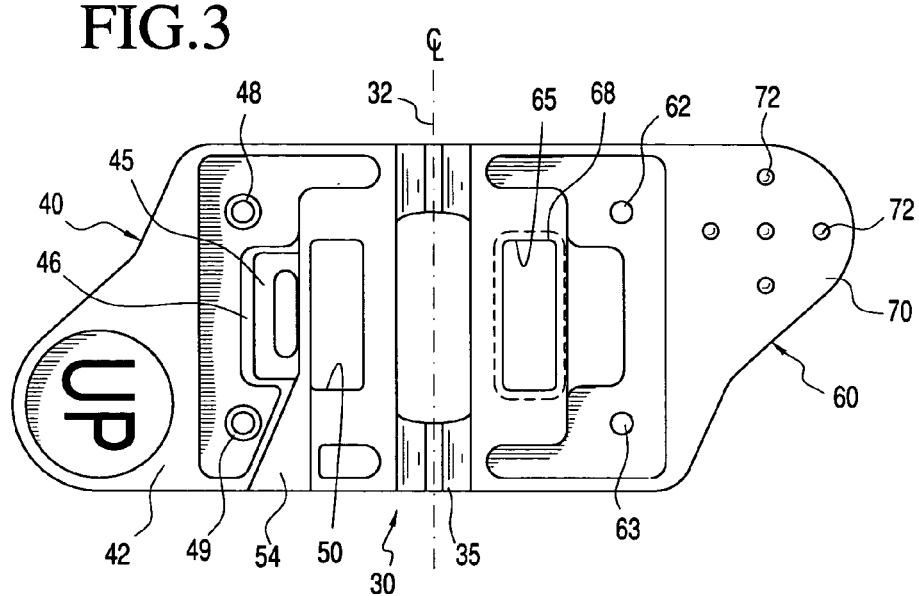
FIG. 3 is a plan view of the case in fully extended planar position.
Figure 4:
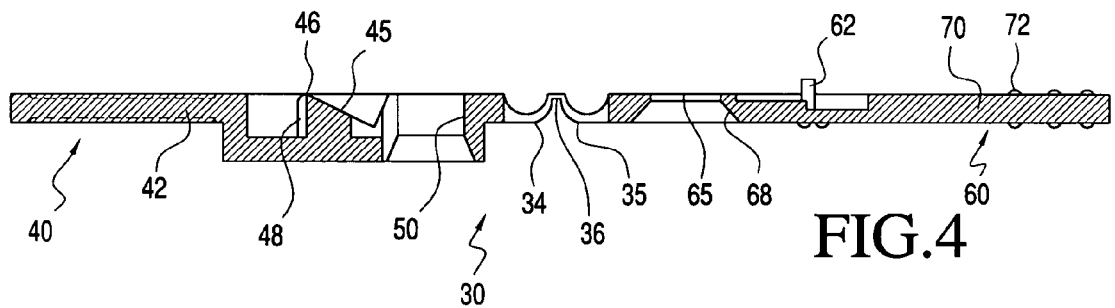
FIG. 4 is a side cross-sectional view of the case of FIGS. 1–3 in the same planar position as in FIG. 3.
Figure 5:
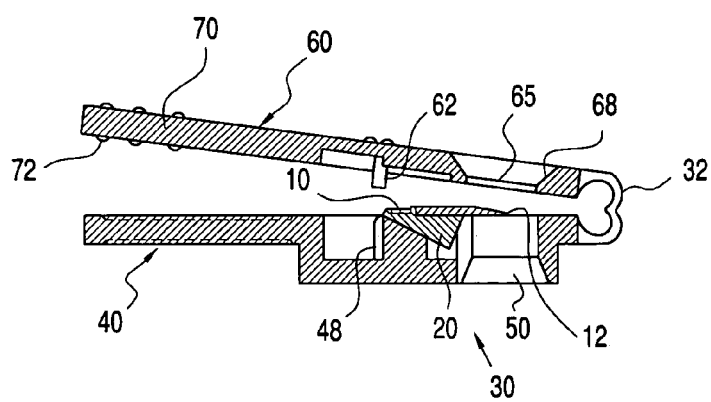
FIG. 5 is a side sectional view of the protective case of FIGS. 1 to 4, showing the case containing a blade and driver and with the two halves substantially but not completely closed.

The body of a case 30 for the blade 10 may be molded of a single unitary part of suitable synthetic resin such as polyvinyl. Although two or more pieces can be employed the angle molded part has cost and convenience advantages. The two halves of the case 30 are hinged about an integral hinge line 32 formed by two curved segments 34, 35 joined by a small but adequately strong central hinge or spine 36 (FIG. 4). The two major halves of the case 30 extend oppositely from the central hinge 36, but are not symmetrical. As seen in FIG. 3, what is to be the lower part 40 of the case 30 includes a wing-shaped clasp 42 extending from its periphery opposite the hinge 36, on which is imprinted an embossed or relief pattern designating "up", for the guidance of the surgeon. This lower half 40 includes an angled driver recess 44 (the internal angle, which mates with the triangular cross-section of the driver 20, is best seen in FIGS. 4 and 5) within a raised border 46. Two adjacent postholes 48, 49 are positioned to receive pins for securing the halves together, although other frictional retaining elements can be used for releasable clamping. On the opposite side of the driver recess 44 is a lower window 50, the midregion of which is in alignment with the cutting edge 12 of the microkeratome blade 10 when installed. This relationship is illustrated most clearly in FIGS. 2 and 5.

Figure 2:
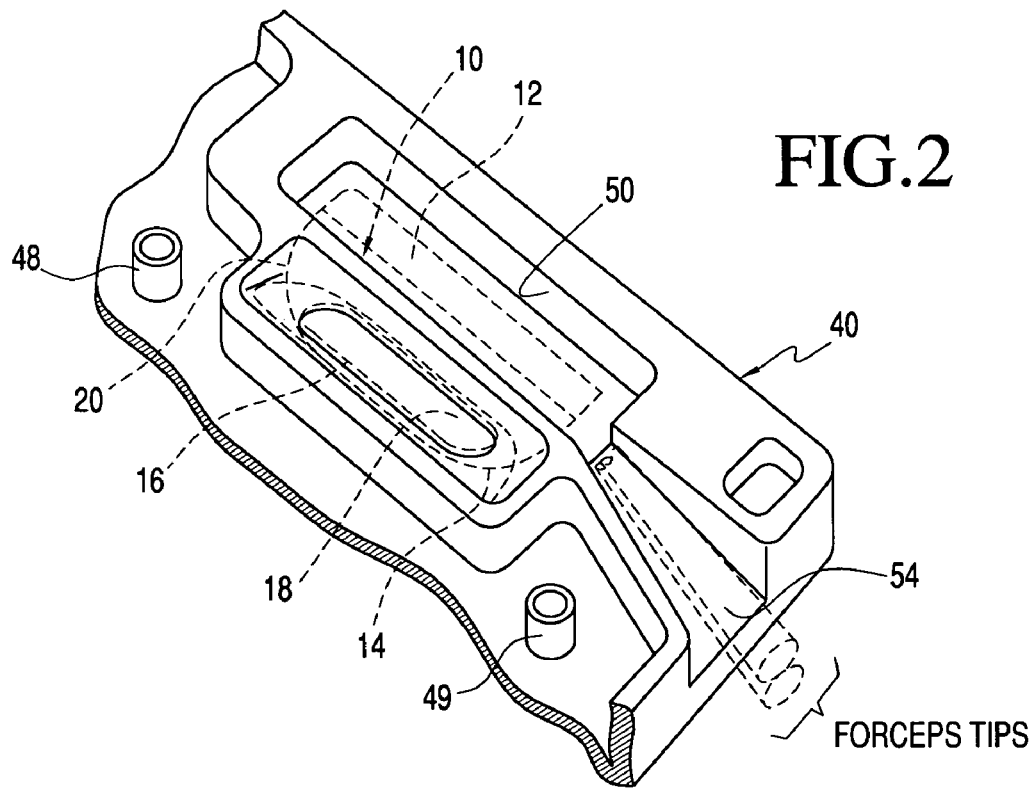
FIG. 2 is an enlarged fragmentary perspective view of the blade and driver (shown in phantom) as mounted in the case for removal by forceps tips within a converging side access guide surface.

At one side of the driver recess 44 and the window 50 a converging forceps ramp 54 (FIGS. 1–3 particularly) that converges on three sides extends inwardly from one side of the lower half 40 toward a space immediately adjacent side of the inserted blade 10, as seen in FIG. 2. The forceps ramp 54 angles upwardly as the sides converge to the side of the blade 10, so that with an open forceps the surgeon need only insert the tip portion into the forceps ramp 54 and follow the inclined surface to engage the blade 10 behind its cutting edge 12.

On the opposite side of the case 30 from the centerline 32, the upper half 60 of the body includes a pair of pins 62, 63 each positioned, when the hinged assembly is closed, to engage in a different one of the post holes, 48, 49. At closure a window 65 in the face of the upper half 60 encompasses the cutting edge 12 of the blade 10 providing visual and physical access from this side as well. The upper half of the upper window 65 includes a beveled edge 68 (see FIGS. 4 and 5) to facilitate access to the cutting edge 12 for inspection and/or safeguarding sterilization. When the two halves 40, 60 of the case 30 are closed together, the pins 62, 63 fit in the postholes 48, 49 with a light press fit. A wing-shaped clasp 70 on the upper half 60 of the case 30 includes raised dimples 72 which provide surface irregularities which aid in finger control of the wing clasps 42, 70 during both opening and closing.

It can thus be seen that a relatively low cost blade case is provided that has all the desired attributes, namely secure retention of a protected blade in position, with the blade and holder being fully visually inspectable from both sides, as well as accessible for cleaning and sterilization if desired, but at the same time so designed as to allow a surgeon to seize and remove the blade in simple but assured fashion.

Although there have been described above various forms and modifications in accordance with the invention, the invention encompasses all variations and versions within the scope of the appended claims.

What is claimed is:

1. A case for protecting a small microkeratome blade unit having a precise and delicate front cutting edge and a driver element spaced apart from the cutting edge, the case functioning in a manner to allow the cutting edge to be inspected and cleaned on either side while still protected, but making the blade unit still readily accessible for a surgeon's forceps, comprising:

a double-walled case including a front edge hinge, the walls having dissimilar interior configurations within peripheries which encompass the periphery of the blade unit, wherein a first wall includes an inner recess shaped to receive at least a portion of the driver of the blade unit with the cutting edge substantially parallel to the front edge of the case, and also including a window surrounding the cutting edge and providing access to the cutting edge from the exterior;

the second wall including an inner boss engaging the opposite side of the blade unit located in position in the recess of the opposite wall when the walls are brought together, the second wall also including a window surrounding the cutting edge and providing access to the cutting edge from the exterior, and wherein the second wall includes a forceps guideway extending between the exterior of the second wall to a region of the blade unit adjacent to but spaced from the cutting edge.

2. A case as set forth in claim 1 above, wherein the forceps guideway extends from a side of the case spaced from the front hinge inwardly to the region of the blade unit and includes converging tapers in two dimensions from the exterior into the blade unit for guiding the tip of a forceps inserted from the side.

3. A case as set forth in claim 2 above wherein the case is a unitary molded unit having an integral hinge structure between the first and second walls, and wherein the windows surrounding the cutting edge have peripheral exterior peripheries, the case further including frictional elements extending in from the interior surfaces of the walls for detachably engaging to hold the walls in the closed position.

4. A device for accessibly retaining a microkeratome blade unit having a cutting edge, in which the blade unit includes a driver element engaged to the blade at a spacing from the cutting edge, the device comprising:

a blade case configured in two halves and including a flexible hinge joining the two halves along a front edge thereof, the two halves being configured to retain the blade unit therein in an interior position, with the cutting edge substantially parallel to the front edge of the case, a first half of the case including an interior recess for receiving at least a portion of the driver with the cutting edge in position relative to the front edge of the case, and the second half of the case including a boss for retaining the blade unit with the driver portion in the recess, when the walls are together, the first and second halves each including open windows positioned to encompass the cutting edge of the blade unit for inspection and cleaning and the first half of the blade unit including a guide groove from a side of the first wall into a side region of a retained blade unit, whereby when the halves of the case are opened, a forceps can be inserted along the guide groove to engage the blade unit behind the cutting edge.

5. A device as set forth in claim 4 above, wherein each of the halves includes extending wing elements along the edge opposite the front edge, the wing elements being displaced laterally along the edge relative to each other to provide manual engagement surfaces for opening on closing the case, and wherein the opposite halves include mating frictional elements for holding the halves in closed position.

6. A case as set forth in claim 5 above, wherein the case comprises a unitary element including a hinge mechanism joining the two halves, and wherein the recess in the first half comprises a concavity shaped to receive a portion of the driver element of the blade unit.

7. A case as set forth in claim 6 above, wherein the wing elements are spaced apart laterally relative to the rear edges of the halves, wherein one of the wing elements includes indicia to designate the orientation of the case, and wherein the case is of polyvinyl material.

8. A case as set forth in claim 6 above, wherein the frictional elements for retaining the halves in engaged position comprise postholes in one of the halves extending in the direction of the other half and pins extending from the other half and positioned to engage in the postholes when the halves are in engaged position.

9. The case as set forth in claim 8 above, wherein the guide groove comprises a converging forceps ramp and wherein the windows encompassing the cutting edge of the blade include beveled exterior peripheral surfaces.

* * * * *